(12) United States Patent
Matsumoto

(10) Patent No.: US 6,521,567 B2
(45) Date of Patent: Feb. 18, 2003

(54) HERBICIDAL COMPOSITION

(75) Inventor: Hiroshi Matsumoto, Kakogawa (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/046,704

(22) Filed: Jan. 17, 2002

(65) Prior Publication Data

US 2002/0137630 A1 Sep. 26, 2002

(30) Foreign Application Priority Data

Jan. 22, 2001 (JP) ........................................ 2001-013454

(51) Int. Cl.⁷ ........................ A01N 43/38; A01N 57/02; A01N 57/10
(52) U.S. Cl. ...................................... 504/128; 504/138
(58) Field of Search ................... 504/128, 138

(56) References Cited

U.S. PATENT DOCUMENTS

| | | | |
|---|---|---|---|
| 4,640,707 A | 2/1987 | Nagano et al. | 71/96 |
| 4,770,695 A | 9/1988 | Nagano et al. | 71/96 |
| 5,062,884 A | 11/1991 | Plath et al. | 71/95 |

Primary Examiner—S. Mark Clardy
(74) Attorney, Agent, or Firm—Birch, Stewart, Kolasch & Birch, LLP

(57) ABSTRACT

An application of an N-phenyltetrahydrophthalimide compound represented by Chemical Formula (1):

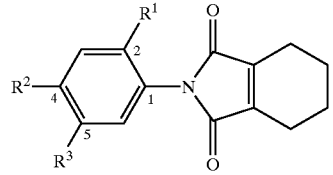

(Chemical Formula 1)

wherein $R^1$ represents hydrogen or halogen; $R^2$ represents halogen and $R^3$ represents hydrogen, (C1–C8 alkoxy) carbonyl C1–C2 alkoxy, C1–C6 alkynyloxy or (C1–C8 alkoxy)carbonyl C2–C3 haloalkenyl, or $R^2$ and $R^3$ represent together —O—CHR⁴—C(=O)—NR⁵—, whose oxygen connected to 4-position of the benzene ring, whose nitrogen connected to 5-position of the benzene ring and wherein $R^4$ represents hydrogen or methyl and $R^5$ represents C1–C6 alkyl, C3–C6 alkenyl, C3–C6 alkynyl or (C1–C3 alkoxy) C1–C3 alkyl, with an effective amount of an insecticidal organophosphorus compound against weeds can attain higher herbicidal effect than an application of said N-phenyltetrahydrophthalimide compound alone.

12 Claims, No Drawings

HERBICIDAL COMPOSITION

TECHNICAL FIELD

The present invention relates to a new herbicidal composition.

BACKGROUND ART

At the present time, it is known that an N-phenyltetrahydrophthalimide compound represented by Chemical Formula (1) described below has herbicidal activity (See U.S. Pat. No. 4,770,695, U.S. Pat. No. 4,640,707, U.S. Pat. No. 5,062,884 and so on).

In a field of herbicide, requested are how can an application of less amount of herbicide attain same herbicidal effect as an application of usual amount of it.

DISCLOSURE OF INVENTION

The present inventor has intensively studied to find out a method for boosting herbicidal activity of the N-phenyltetrahydrophthalimide compound. As a result he has found that, when the N-phenyltetrahydrophthalimide compound was applied with an insecticidal organophosphorus compound, the herbicidal activity of the N-phenyltetrahydrophthalimide compound against weeds was higher than when the N-phenyltetrahydrophthalimide compound was solely applied.

Thus, the present invention provides a herbicidal composition of the N-phenyltetrahydrophthalimide compound represented by Chemical Formula (1):

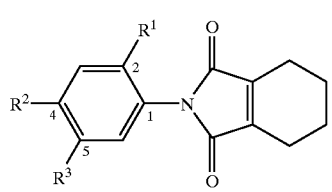

(Chemical Formula 1)

wherein $R^1$ represents hydrogen or halogen; $R^2$ represents halogen and $R^3$ represents hydrogen, (C1–C8 alkoxy) carbonyl C1–C2 alkoxy, C1–C6 alkynyloxy or (C1–C8 alkoxy)carbonyl C2–C3 haloalkenyl, or $R^2$ and $R^3$ represent together —O—CHR$^4$—C(=O)—NR$^5$—, whose oxygen connected to 4-position of the benzene ring, whose nitrogen connected to 5-position of the benzene ring, wherein $R^4$ represents hydrogen or methyl and $R^5$ represents C1–C6 alkyl, C3–C6 alkenyl, C3–C6 alkynyl or (C1–C3 alkoxy) C1–C3 alkyl, and an effective amount for increasing herbicidal activity of the N-phenyltetrahydrophthalimide compound of an insecticidal organophosphorus compound (hereinafter, referred to as the present composition); and a method for controlling weeds which comprises of applying said N-phenyltetrahydrophthalimide compound with the insecticidal organophosphorus compound to weeds or to a place where weeds are growing or will grow (hereinafter referred to as the present method).

The N-phenyltetrahydrophthalimide compound represented by Chemical Formula (1) (hereinafter referred to as the present imide compound) includes the compounds described below.

A compound wherein $R^2$ and $R^3$ are together —O—CHR$^4$—C(=O)—NR$^5$— in Chemical Formula (1), that is represented by Chemical Formula (4):

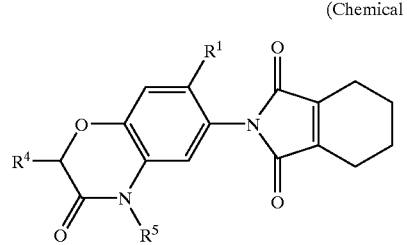

(Chemical Formula 4)

wherein $R^1$, $R^4$ and $R^5$ are as defined above;

a compound wherein $R^1$ is fluorine in Chemical Formula (4);

a compound wherein $R^4$ is hydrogen in Chemical Formula (4);

a compound wherein $R^5$ is C3–C6 alkynyl in Chemical Formula (4);

a compound wherein $R^1$ is fluorine, $R^4$ is hydrogen and $R^5$ is C3–C6 alkynyl in Chemical Formula (4);

a compound wherein $R^2$ is $R^{21}$ and $R^3$ is $R^{31}$ in the Chemical Formula (1), that is represented by Chemical Formula (5):

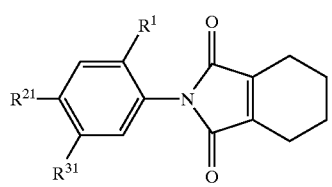

(Chemical Formula 5)

wherein $R^1$ are as defined above, $R^{21}$ represents halogen and $R^{31}$ represents hydrogen, (C1–C8 alkoxy)carbonyl C1–C2 alkoxy, C1–C6 alkynyloxy or (C1–C8 alkoxy)carbonyl C2–C3 haloalkenyl;

a compound wherein $R^1$ is fluorine in Chemical Formula (5);

a compound wherein $R^{21}$ is chlorine in Chemical Formula (5);

a compound wherein $R^{31}$ is (C1–C8 alkoxy)carbonyl C1–C2 alkoxy in Chemical Formula (5);

a compound wherein $R^{31}$ is C1–C6 alkynyloxy in Chemical Formula (5);

a compound wherein $R^{31}$ is (C1–C8 alkoxy)carbonyl C2–C3 haloalkenyl in Chemical Formula (5);

a compound wherein $R^1$ is fluorine, $R^{21}$ is chlorine and $R^{31}$ is (C1–C8 alkoxy)carbonyl C1–C2 alkoxy in Chemical Formula (5).

Furthermore, the present imide compound includes the compounds described below.

N-(7-fluoro-3,4-dihydro-3-oxo-4-prop-2-ynyl-2H-1,4-benzoxazin-6-yl)cyclohex-1-ene-1,2-dicarboxamide (Chemical Formula 7)

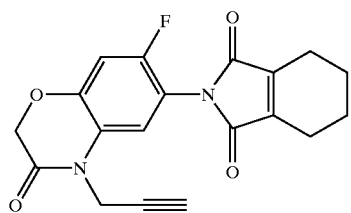

(common name: flumioxazin);
pentyl[2-chloro-5-(cyclohex-1-ene-1,2-dicarboximido)-4-fluorophenoxy]acetate (Chemical Formula 8)

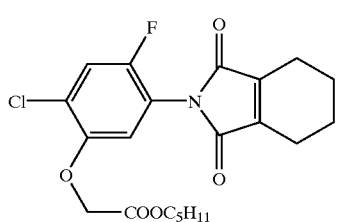

(common name: flumiclorac-pentyl);
(Z)-ethyl 2-chloro-3-[2-chloro-5-(cyclohex-1-ene-1,2-dicarboximido)phenyl]acrylate (Chemical Formula 9)

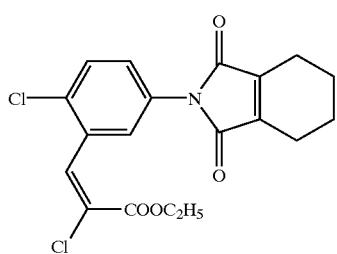

(common name: cinidon-ethyl);
N-(4-chlorophenyl)cyclohex-1-ene-1,2-dicarboxamide (Chemical Formula 10)

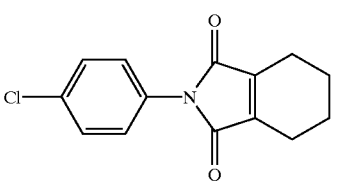

(common name: chlorphthalim).

The insecticidal organophosphorus compound in the present invention includes, for example, the compounds described below.

A compound represented by Chemical Fonnula (6):

(Chemical Formula 6)

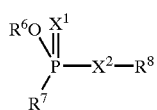

wherein $X^1$ represents oxygen or sulfur, $X^2$ represents oxygen, sulfur or direct bond between phosphorous atom and $R^8$, $R^6$ represents lower alkyl, $R^7$ represents lower alkoxy, lower alkylthio, lower alkylcarbonylamino or phenyl, $R^8$ represents optionally substituted alkyl, optionally substituted alkenyl, optionally substituted phenyl or optionally substituted heteroaryl;

a compound wherein $X^1$ is sulfur, $X^2$ is oxygen, $R^6$ is C1–C4 alkyl, $R^7$ is C1–C4 alkylcarbonylamino and $R^8$ is optionally substituted C1–C4 alkyl in the Chemical Formula (6);

a compound wherein $X^1$ is sulfur, $X^2$ is sulfur, $R^6$ is C1–C4 alkyl, $R^7$ is C1–C4 alkoxy and $R^8$ is optionally substituted C1–C4 alkyl in the Chemical Formula (6);

a compound wherein $X^1$ is sulfur, $X^2$ is oxygen, $R^6$ is C1–C4 alkyl, $R^7$ is C1–C4 alkoxy and $R^8$ is optionally substituted alkenyl in the Chemical Formula (6);

a compound wherein $X^1$ is sulfur, $X^2$ is oxygen, $R^6$ is C1–C4 alkyl, $R^7$ is C1–C4 alkoxy and $R^8$ is optionally substituted phenyl in the Chemical Formula (6);

a compound wherein $X^1$ is sulfur, $X^2$ is oxygen, $R^6$ is C1–C4 alkyl, $R^7$ is C1–C4 alkylthio and $R^8$ is optionally substituted phenyl in the Chemical Formula (6);

a compound wherein $X^1$ is sulfur, $X^2$ is oxygen, $R^6$ is C1–C4 alkyl, $R^7$ is C1–C4 alkoxy and $R^8$ is optionally substituted pyrimidinyl in the Chemical Formula (6);

a compound wherein $X^1$ is sulfur, $X^2$ is oxygen, $R^6$ is C1–C4 alkyl, $R^7$ is C1–C4 alkoxy and $R^8$ is optionally substituted pyridyl in the Chemical Formula (6);

a compound wherein $X^1$ is sulfur, $X2$ is oxygen, $R^6$ is C1–C4 alkyl, $R^7$ is C1–C4 alkoxy and $R^8$ is optionally substituted isoxazolyl in the Chemical Formula (6).

Furthermore, the insecticidal organophosphorus compound includes the compounds described below.

O,O-dimethyl O-4-nitro-m-tolyl phosphorothioate (common name: fenitrothion);

O,O-dimethyl O-4-methylthio-m-tolyl phosphorothioate (common name: fenthion);

O,O-diethyl O-2-isopropyl-6-methylpyrimidin-4-yl phosphorothioate (common name: diazinon);

O,O-diethyl O-3,5,6-trichloro-2-pyridyl phosphorothioate (common name: chlorpyrifos);

O,S-dimethyl acetylphosphoramidothioate (common name: acephate);

S-2,3-dihydro-5-methoxy-2-oxo-1,3,4-thiadiazol-3-ylmethyl O,O-dimethyl phosphorodithioate (common name: methidathion);

O,O-diethyl S-2-ethylthioethyl phosphorodithioate (common name: disulfoton);

2,2-dichlorovinyl dimethyl phosphate (common name: dichlorvos);

O-ethyl O-4-(methylthio)phenyl S-propyl phosphorodithioate (common name: sulprofos);

O-4-cyanophenyl O,O-dimethyl phosphorothioate (common name: cyanophos);

O,O-dimethyl S-methylcarbamoylmethyl phosphorodithioate (common name: dimethoate);

S-α-ethoxycarbamoylbenzyl O,O-dimethyl phosphorodithioate (common name: phenthoate);

diethyl (dimethoxythiophosphorylthio)succinate (common name: malathion);

dimethyl 2,2,2-trichloro-1-hydroxyethylphosphonate (common name: trichlorfon);

S-(3,4-dihydro-4-oxobenzo[d]-[1,2,3]-triazin-3-ylmethyl) O,O-dimethyl phosphorodithioate (common name: azinphos-methyl);

dimethyl (E)-1-methyl-2-(methylcarbamoyl)vinyl phosphate (common name: monocrotophos);

O,O,O',O'-tetraethyl S,S'-methylene bis(phosphorodithioate) (common name: ethion);

S-2-ethylthioethyl O,O-dimethyl phosphorodithioate (common name: thiometon);

O,O-diethyl O-(5-phenyl-1,2-oxazol-3-yl) phosphorothioate (common name: isoxathion);

O,O-dimethyl S-2-(1-methylcarbamoylethylthio)ethyl phosphorothioate (common name: vamidothion);

O-2,4-dichlorophenyl O-ethyl S-propyl phosphorodithioate (common name: prothiofos);

S-2-ethylsulfinyl-1-methylethyl] O,O-dimethyl phosphorothioate (common name: xydeprofos).

The present imide compound can be produced according to the procedures described, for example, in U.S. Pat. No. 4,770,695, U.S. Pat. No. 4,640,707, U.S. Pat. No. 5,062,884 and the others.

The present composition has herbicidal activity in the foliar treatment and the soil treatment on upland field against various weeds such as listed below.

Polygonaceous weeds:
wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceous weeds:
common purslane (*Portulaca oleracea*)

Caryophyllaceous weeds:
common chickweed (*Stellaria media*)

Chenopodiaceous weeds:
common lambsquarters (*Chenopodium album*), kochia (*Kochia scoparia*)

Amaranthaceous weeds:
redroot pigweed (*Amaranthus retroflexus*), smooth pigweed (*Amaranthus hybridus*)

Cruciferous (*brassicaceous*) weeds:
wild radish (*Raphanus raphanistrum*), wild mustard (*Sinapis arvensis*), shepherdpurse (*Capsella bursa-pastoris*)

Leguminous (*fabaceous*) weeds:
hemp sesbania (*Sesbania exaltata*), sicklepod (*Cassia obtusifolia*), Florida beggarweed (*Desmodium tortuosum*), white clover (*Trifolium repens*), common vetch (*Vicia sativa*)

Malvaceous weeds:
velvetleaf (*Abutilon theophrasti*), prickly sida (*Sida spinosa*)

Violaceous weeds:
field pansy (*Viola arvensis*), wild pansy (*Viola tricolor*)

Rubiaceous weeds:
catchweed bedstraw (*cleavers*) (*Galium aparine*)

Convolvulaceous weeds:
ivyleaf morningglory (*Ipomoea hederacea*), tall morningglory (*Ipomoea purpurea*), entireleaf morningglory (*Ipomoea hederacea* var. integriuscula), pitted morningglory (*Ipomoea lacunosa*), field bindweed (*Convolvulus arvensis*)

Labiate weeds:
purple deadnettle (*Lamium purpureum*), henbit (*Lamium amplexicaule*)

Solanaceous weeds:
jimsonweed (*Datura stramonium*), black nightshade (*Solanum nigrum*)

Geraniaceae weeds:
Carolina geranium (*Geranium carolinianum*)

Scrophulariaceous weeds:
birdseye speedwell (*Veronica persica*), ivyleaf speedwell (*Veronica hederaefolia*)

Composite weeds:
common cocklebur (*Xanthium strumarium*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)

Boraginaceous weeds:
forget-me-not (*Myosotis arvensis*)

Asclepiadaceous weeds:
common milkweed (*Asclepias syriaca*)

Euphorbiaceous weeds:
sun spurge (*Euphorbia helioscopia*), spotted spurge (*Euphorbia maculata*)

Graminaceous weeds:
barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)

Commelinaceous weeds:
Asiatic dayflower (*Commelina communis*)

Equisetaceous weeds:
field horsetail (*Equisetum arvense*)

Cyperaceous weeds:
rice flatsedge (*Cyperus iria*), purple nutsedge (Cyperus rotundus), yellow nutsedge (*Cyperus esculentus*)

Furthermore, the present composition also has herbicidal activity in flooding treatment of paddy fields against various weeds such as listed below.

Graminaceous weeds:
barnyardgrass (*Echinochloa oryzoides*)

Scrophulariaceous weeds:
common false pimpernel (*Lindernia procumbens*)

Lythraceae weeds:
Indian toothcup (*Rotala indica*), redstem (*Ammannia multiflora*)

Elatinaceae weeds:
waterwort (*Elatine triandra*)

Cyperaceae weeds:
smallflower umbrella sedge (*Cyperus difformis*), hardstem bulrush (Scirpus juncoides subsp. hotarui), needle spikerush (*Eleocharis acicularis*), nutsedge sp. (*Cyperus serotinus*), water chestnut (*Eleocharis kuroguwai*)

Pontederiaceae weeds:
Monochoria (*Monochoria vaginalis*)

Alismataceae weeds:
dwarf arrowhead (*Sagittaria pygmaea*), arrowhead (*Sagittaria trifolia*), waterplantain (*Alisma canaliculatum*)

Potamogetonaceae weeds:
roundleaf pondweed (*Potamogeton distincutus*)

Umbelliferae weeds:
water dropwort sp. (*Oenanthe javanica*)

The present composition can also be used to control a wide variety of weeds which are growing or will grow in non-cultivated lands such as a levee, riverbed, roadside, railroad, green field area of a park, ground, parking area, airport, industrial place (ex. factory, storage equipment), fallow field, idle land of an urban area; wood lot, grasslands, lawns, forests, and the like. The present composition also has herbicidal activity against various aquatic weeds, such as water hyacinth (*Eichhornia crassipes*), which are growing or will grow at rivers, canals, waterways reservoirs and the like.

In the present composition, the mixing ratio of the insecticidal organophosphorus compound to the present imide compound, it may vary within a range which the herbicidal activity of the present imide compound can be increased, is usually 0.1:1 to 10000:1, preferably 1:1 to 500:1, more preferably 1:1 to 100:1, much more preferably 2:1 to 25:1 by weight.

The present composition may be usually used in the form of formulations such as emulsifiable concentrates, wettable powders, flowables, granules and the like which can be prepared by mixing with solid carriers, liquid carriers, and the like, and if necessary, adding surfactants, other adjuvants and the like.

In such a formulation, the present imide compound and the insecticidal organophosphorus compound are usually contained at the total amount of 10 to 80% by weight.

The solid carrier to be used in the formulation may include, for example, the following materials in fine powder or granule form: clays (e.g., kaolinite, diatomaceous earth, synthetic hydrated silicon oxide, Fubasami clay, bentonite, acid clay); talc and other inorganic minerals (e.g., sericite, powdered quartz, powdered sulfur, activated carbon, calcium carbonate); and chemical fertilizers (e.g., ammonium sulfate, ammonium phosphate, ammonium nitrate, ammonium chloride, urea). The liquid carrier may include, for example, water; alcohols (e.g., methanol, ethanol); ketones (e.g., acetone, methyl ethyl ketone, cyclohexanone); aromatic hydrocarbons (e.g., toluene, xylene, ethylbenzene, methylnaphthalene); non-aromatic hydrocarbons (e.g., hexane, cyclohexane, kerosine); esters (e.g., ethyl acetate, butyl acetate); nitriles (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloroethylene).

The surfactant may include, for example, alkylsulfric acid esters; alkylsulfonic acid salts; alkylarylsulfonic acid salts; their polyoxyethylene derivatives; polyethylene glycol ethers; polyhydric alcohol esters; and sugar alcohol derivatives.

The other adjuvants may include, for example, adhesive agents and dispersing agents, such as casein, gelatin, polysaccharides (e.g., starch, gum arabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-di-tert-butyl-4-methylphenol), BHA (2-/3-tert-butyl-4-methyoxyphenol), vegetable oils, mineral oils, fatty acids, and fatty acid esters.

The present composition can also be prepared by making each of the present imide compound and the insecticidal organophosphorus compound into the above formulations; and then mixing these formulations.

The present composition thus formulated may be applied to weeds or to a place where weeds are growing or will grow as such, or after diluted with water or the like.

Furthermore, the present composition can also be prepared by diluting each formulations of the present imide compound and the insecticidal organophosphorus compound with water or the like; and then mixing these dilutions. Further, the present composition may also be used in admixture or be used together with other herbicides, insecticides, fungicides, plant growth regulators, fertilizers or safener.

The present method is usually carried out by an application of the present composition, as such or after dilution, to weeds or to a place where weeds grow or will grow, and also by application of the present imide compound (or its formulation) and the insecticidal organophosphorus compound (or its formulation) together.

The application amounts of the present imide compound and the insecticidal organophosphorus compound, although they may vary with the mixing ratio of them, weather conditions, formulation types, application times, application methods, application places, and weeds to be controlled, are usually 0.1 to 1000 g for the present imide compound and 0.1 to 10000 g for the insecticidal organophosphorus compound per hectare. In the case of emulsifiable concentrates, wettable powders, flowables, or the like, they are usually applied after diluted in their prescribed amounts with water at a ratio of 100 to 1000 liters per hectare.

The present method can be used, for example, in a corn field, a wheat field, a barley field, a rice field, a sorghum field, a soybean field, a cotton field, a sugar beet field, peanut field, a sunflower field, a rape field, an orchard and a paddy field.

EXAMPLE

The present invention is described in more detail with reference to Formulation examples and Test Examples, but the present invention is not limited to these Examples.

The following will describe formulation examples, in which parts are by weight.

Formulation Example 1

Two and half (2.5) parts of flumiclorac-pentyl, flumioxazin or cinidon-ethyl, 42 parts of fenitrothion, fenthion, diazinon, chlorpyrifos, acephate, methidathion, disulfoton, dichlorvos, sulprofos, cyanophos, dimethoate, phenthoate, malathion, trichlorfon, azinphos-methyl, monocrotophos, ethion, thiometon, isoxathion, vamidothion, prothiofos or oxydeprofos, 50 parts of Solvesso (aromatic hydrocarbon, produced by Exxon Mobil Chemical) and 5.5 parts of Sorpol 3816 (anionic type and non-ionic type surfactants, produced by Toho Chemical) are well stirred and mixed to give each emulsifiable concentrate.

The following will describe test examples.

Evaluation Criteria

The herbicidal effect is evaluated with indices of 0 to 100 at intervals of 5, wherein "0" means that there was no or little difference in the degree of germination or growth between the treated plants and the untreated plants at the time of examination, "100" means that the test plants died completely.

Test Example 1

Fifty (50) parts of flumioxazin, 3 parts of Sorpol 5029-0 (produced by Toho Chemical), 2 parts of Demol SNB and 45 parts of Shokozan Clay were well stirred and mixed to give 50% wettable powders of flumioxazin. From the aqueous dilution of said 50% wettable powders of flumioxazin, with a aqueous dilution of a emulsifiable concentrate of fenitrothione (commercial name: Sumithion EC, produced by Agros), prepared aqueous dilution of the prescribed concentration of the present formulation.

The aqueous dilution of the present formulation, with 1000 liters per hectare, were sprayed over a place in the orchard where common vetch and Carolina geranium (the height: about 40 to 55 cm) were growing. After 9 days from the application, the herbicidal activity were examined. The result are shown in Table 1.

TABLE 1

| Test Compound | Dosage (g/hectare) | Herbicidal activity common vetch | Herbicidal activity Carolina geranium |
| --- | --- | --- | --- |
| flumioxazin | 60 | 10 | 50 |
| flumioxazin + fenitrothione | 60 + 1000 | 70 | 70 |

Test Example 2

Fifty (50) parts of flumioxazin, 3 parts of Sorpol 5029-0 (produced by Toho Chemical), 2 parts of Demol SNB and 45 parts of Shokozan Clay were well stirred and mixed to give 50% wettable powders of flumioxazin. From the aqueous dilution of said 50% wettable powders of flumioxazin, with a aqueous dilution of 40% wettable powders of cyanophos (commercial name: Cyanox WP, produced by Agros), 25% wettable powders of chlorpyrifos (commercial name: Dursban WP, produced by Kumiai Chemical), 50% wettable powders of acephate (commercial name: Ortran WP, produced by Hokko Chemical), 36% wettable powders of methidathion (commercial name: Supracide WP, produced by Kumiai Chemical), 50% emulsifiable concentrate of phenthoate (commercial name: Elsan EC, produced by Nissan Chemical), 40% emulsifiable concentrate of diazinone (commercial name: Diazinon EC, produced by Hokko Chemical) or 50% emulsifiable concentrate of dichlorvos (commercial name: DDVP EC, produced by Takeda Pharmaceutical), prepared each aqueous dilution of the prescribed concentration of the present formulation.

Their aqueous dilution of the present formulation, with 1000 liters per hectare, were sprayed over a place in the field where common cocklebur (the height: about 55 cm) were growing. After 8 days from the application, the herbicidal activity were examined. The result are shown in Table 2.

TABLE 2

| Test Compound | Dosage (g/hectare) | Herbicidal activity |
| --- | --- | --- |
| flumioxazin | 60 | 20 |
| flumioxazin + cyanophos | 60 + 1000 | 75 |
| flumioxazin + chlorpyrifs | 60 + 100 | 70 |
| flumioxazin + acephate | 60 + 1000 | 35 |
| flumioxazin + methidathion | 60 + 1000 | 40 |
| flumioxazin + phenthoate | 60 + 1000 | 70 |
| flumioxazin + diazinone | 60 + 1000 | 80 |
| flumioxazin + dichlorvos | 60 + 1000 | 45 |

Test Example 3

Fifty (50) parts of flumioxazin, 3 parts of Sorpol 5029-0 (produced by Toho Chemical), 2 parts of Demol SNB and 45 parts of Shokozan Clay were well stirred and mixed to give 50% wettable powders of flumioxazin. From the aqueous dilution of said 50% wettable powders of flumioxazin, with a aqueous dilution of 25% emulsifiable concentrate of thiometon (commercial name: Ekatin EC, produced by Sankyo), 45% emulsifiable concentrate of oxydeprofos (commercial name: Estox EC, produced by Nihon Bayer Agrochem), 50% emulsifiable concentrate of isoxathion (commercial name: Karphos EC, produced by Sankyo), 37% liquid of vamidothion (commercial name: Kilval Liq, produced by Nissan Chemical), 45% emulsifiable concentrate of prothiofos (commercial name: Tokuthion EC, produced by Nihon Bayer Agrochem), 50% emulsifiable concentrate of fenthion (commercial name: Baycid EC, produced by Nihon Bayer Agrochem) or 50% emulsifiable concentrate of sulprofos (commercial name: Bolstar EC, produced by Nihon Bayer Agrochem), prepared each aqueous dilution of the prescribed concentration of the present formulation.

Their aqueous dilution of the present formulation, with 1000 liters per hectare, were sprayed over a place in the field where common cocklebur (the height: about 65 cm) were growing. After 4 days from the application, the herbicidal activity were examined. The result are shown in Table 3.

TABLE 3

| Test Compound | Dosage (g/hectare) | Herbicidal activity |
| --- | --- | --- |
| flumioxazin | 60 | 30 |
| flumioxazin + thiometon | 60 + 1000 | 70 |
| flumioxazin + oxydeprofos | 60 + 1000 | 70 |
| flumioxazin + isoxathion | 60 + 1000 | 70 |
| flumioxazin + vamidothion | 60 + 1000 | 65 |
| flumioxazin + prothiofos | 60 + 1000 | 70 |
| flumioxazin + fenthion | 60 + 1000 | 65 |
| flumioxazin + sulprofos | 60 + 1000 | 70 |

Test Example 4

Ten (10) parts of flumiclorac-pentyl were dissolved in 80 parts of xylene, after adding 10 parts of Sorpol 3005X (produced by Toho Chemical), the solution was well stirred and mixed to give 10% emulsifiable concentrate of flumiclorac-pentyl. From the aqueous dilution of said 10% emulsifiable concentrate of flumiclorac-pentyl, with a aqueous dilution of 25% emulsifiable concentrate of thiometon (commercial name: Ekatin EC, produced by Sankyo), 45% emulsifiable concentrate of oxydeprofos (commercial name: Estox EC, produced by Nihon Bayer Agrochem) or 50% emulsifiable concentrate of fenthion (commercial name: baycid EC, produced by Nihon Bayer Agrochem), prepared each aqueous dilution of the prescribed concentration of the present formulation.

Their aqueous dilution of the present formulation, with 1000 liters per hectare, were sprayed over a place in the field where common cocklebur (the height: about 65 cm) were growing. After 4 days from the application, the herbicidal activity were examined. The result are shown in Table 4.

TABLE 4

| Test Compound | Dosage (g/hectare) | Herbicidal activity |
| --- | --- | --- |
| flumiclorac-pentyl | 100 | 30 |
| flumiclorac-pentyl + thiometon | 100 + 1000 | 50 |
| flumiclorac-pentyl + oxydeprofos | 100 + 1000 | 60 |
| flumiclorac-pentyl + fenthion | 100 + 1000 | 70 |

Industrial Applicability

The present composition have excellent herbicidal effect against a variety of weeds.

What is claimed:

1. A herbicidal composition containing:

(i) an N-phenyltetrahydrophthalimide compound represented by Chemical Formula (1):

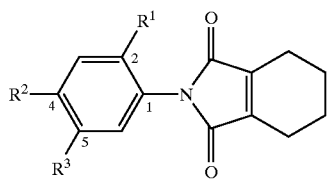

(Chemical Formula 1)

wherein $R^1$ represents hydrogen or halogen; $R^2$ represents halogen and $R^3$ represents hydrogen, (C1–C8 alkoxy)carbonyl C1–C2 alkoxy, C1–C6 alkynyloxy or (C1–C8 alkoxy)carbonyl C2–C3 haloalkenyl, or $R^2$ and $R^3$ represent together —O—CHR$^4$—C(=O)—NR$^5$—, whose oxygen connected to 4-position of the benzene ring, whose nitrogen connected to 5-position of the benzene ring and wherein $R^4$ represents hydrogen or methyl and $R^5$ represents C1–C6 alkyl, C3–C6 alkenyl, C3–C6 alkynyl or (C1–C3 alkoxy) C1–C3 alkyl, and (ii) an effective amount for increasing activity of the N-phenyltetrahydrophthalimide compound of an insecticidal organophosphorus compound.

2. The herbicidal composition according to claim 1, wherein a weight ratio of the insecticidal or ganophosphorus compound to the N-phenyltetrahydrophthalimide compound is 0.1:1 to 10000:1.

3. The herbicidal composition according to claim 1, wherein $R^1$ is hydrogen or fluorine, $R^2$ and $R^3$ are together —O—CH$_2$—C(=O)—NR$^5$—, in which $R^5$ is C3–C6 alkynyl.

4. The herbicidal composition according to claim 1, wherein $R^1$ is fluorine, $R^2$ is chlorine and $R^3$ is (C1–C8 alkoxy)carbonyl C1–C2 alkoxy.

5. The herbicidal composition according to claim 1, wherein the N-phenyltetrahydrophthalimide compound is flumioxazin, flumiclorac-pentyl or cinidon-ethyl.

6. The herbicidal composition according to claim 1, wherein the insecticidal organophosphorus compound is represented by Chemical Formula (6):

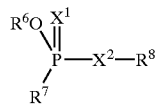

(Chemical Formula 6)

wherein $X^1$ represents oxygen or sulfur, $X^2$ represents oxygen, sulfur or direct bond between phosphorous atom and $R^8$ in the Chemical Formula (6), $R^6$ represents lower alkyl, $R^7$ represents lower alkoxy, lower alkylthio, lower alkylcarbonylamino or phenyl, $R^8$ represents optionally substituted alkyl, optionally substituted alkenyl, optionally substituted phenyl or optionally substituted heteroaryl.

7. The herbicidal composition according to claim 1, wherein the insecticidal organophosphorus compound is fenitrothion, fenthion, diazinon, chlorpyrifos, acephate, methidathion, disulfoton, dichlorvos, sulprofos, cyanophos, dimethoate, phenthoate, malathion, trichlorfon, azinphos-methyl, monocrotophos, ethion, thiometon, isoxathion, vamidothion, prothiofos or oxydeprofos.

8. A method for controlling weeds, which comprises applying (i) an N-phenyltetrahydrophthalimide compound represented by Chemical Formula (1):

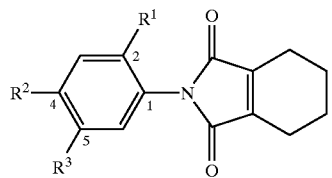

(Chemical Formula 1)

wherein $R^1$ represents hydrogen or halogen; $R^2$ represents halogen and $R^3$ represents hydrogen, (C1–C8 alkoxy)carbonyl C1–C2 alkoxy, C1–C6 alkynyloxy or (C1–C8 alkoxy)carbonyl C2–C3 haloalkenyl, or $R^2$ and $R^3$ represent together —O—CHR$^4$—C(=O)—NR$^5$—, whose oxygen connected to 4-position of the benzene ring, whose nitrogen connected to 5-position of the benzene ring and wherein $R^4$ represents hydrogen or methyl and $R^5$ represents C1–C6 alkyl, C3–C6 alkenyl, C3–C6 alkynyl or (C1–C3 alkoxy) C1–C3 alkyl, with (ii) an effective amount for increasing activity of the N-phenyltetrahydrophthalimide compound of the insecticidal organophosphorus compound,
      to weeds or to a place where weeds are growing or will grow.

9. The method for controlling weeds according to claim 8, wherein a weight ratio of the insecticidal organophosphorus compound to the N-phenyltetrahydrophthalimide compound is from 0.1:1 to 10000:1.

10. The method according to claim 8, wherein $R^1$ is hydrogen or fluorine, $R^2$ and $R^3$ are together —O—CH$_2$—C(=O)—NR$^5$—, in which $R^5$ is C3–C6 alkynyl.

11. The method according to claim 8, wherein $R^1$ is fluorine, $R^2$ is chlorine and $R^3$ is (C1–C8 alkoxy)carbonyl C1–C2 alkoxy.

12. The method according to claim 8, wherein the insecticidal organophosphorus compound is represented by Chemical Formula (6):

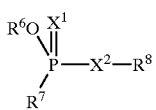

(Chemical Formula 6)

wherein $X^1$ represents oxygen or sulfur, $X^2$ represents oxygen, sulfur or direct bond between phosphorous atom and $R^8$ in the Chemical Formula (6), $R^6$ represents lower alkyl, $R^7$ represents lower alkoxy, lower alkylthio, lower alkylcarbonylamino or phenyl, $R^8$ represents optionally substituted alkyl, optionally substituted alkenyl, optionally substituted phenyl or optionally substituted heteroaryl.

* * * * *